United States Patent

Garrett et al.

[11] Patent Number: 5,414,149
[45] Date of Patent: May 9, 1995

[54] COLOR STABLE BISPHENOLS

[75] Inventors: Dennis Garrett, Evansville; Mitch Reynolds, Wadesville; John Vanbuskirk, Evansville, all of Ind.

[73] Assignee: General Electric Company, Pittsfield, Mass.

[21] Appl. No.: 204,716

[22] Filed: Mar. 2, 1994

[51] Int. Cl.[6] .............................................. C07C 37/88
[52] U.S. Cl. .................... 568/724; 568/722; 568/723
[58] Field of Search ............... 568/702, 703, 722, 724, 568/723

[56] References Cited

U.S. PATENT DOCUMENTS

| | | | |
|---|---|---|---|
| 2,672,485 | 3/1954 | Menn et al. | 568/702 |
| 3,403,186 | 9/1968 | Schlichting et al. | 568/702 |
| 4,191,843 | 3/1980 | Kwantes et al. | 568/728 |
| 4,766,254 | 8/1988 | Faler et al. | 568/724 |
| 4,847,433 | 7/1989 | Kissinger | 568/727 |
| 4,894,486 | 1/1990 | Neil, Jr. et al. | 568/702 |
| 5,124,490 | 6/1992 | Cipullo | 568/758 |
| 5,146,007 | 9/1992 | Cipullo | 568/727 |

FOREIGN PATENT DOCUMENTS

| | | | |
|---|---|---|---|
| 7450 | 3/1967 | Japan | 568/703 |
| 717634 | 10/1954 | United Kingdom | 568/703 |

*Primary Examiner*—Werren B. Lone

[57] ABSTRACT

Bisphenols, such as bisphenol-A are color-stabilized by the addition of an α-hydroxy polycarboxylic acid iron sequestrant.

9 Claims, No Drawings

COLOR STABLE BISPHENOLS

BACKGROUND OF THE INVENTION

1. Field of The Invention

The invention relates to bisphenol compounds and color stable compositions.

2. Brief Description of The Prior Art

Bisphenols are a valuable class of organic compounds employed in a wide variety of applications. Commercial preparation of the bisphenols frequently involves reacting 2 moles of a starting phenol reactant with a carbonyl compound under acid catalyst conditions. For example, the dihydric phenol 2,2 bis(p-hydroxyphenyl) propane (commonly referred to as "bisphenol-A") is commercially prepared by condensing 2 moles of phenol with a mole of acetone in the presence of an acid catalyst. The phenol is present in a molar excess of the stoichiometric requirement. During the condensation, a number of by-products are formed which are contaminants of the desired product, bisphenol-A. These contaminants, carried in the product stream from the condensation reaction zone, include water, trace quantities of acidic materials derived from the catalyst, unreacted phenol and acetone and a number of isomers of bisphenol-A.

Invariably, there are also carried in the product stream trace amounts of metals introduced with reactants or from the apparatus for reaction.

Although very sophisticated procedures have been developed for separating contaminants from the desired bisphenol products and purifying those products, complete elimination would add substantially to the production costs. Therefore, traces of many of these contaminants have been tolerated to a degree.

Representative of methods and process for the preparation of bisphenols are those described in the U.S. Pat. Nos. 4,191,843; 4,766,254; 4,847,433; 5,124,490; and 5,146,007, all of which are incorporated herein by reference thereto.

One contaminant of the bisphenols, such as bisphenol-A, occurs during storage and after preparation. Color bodies result from thermal oxidative reactions of certain phenolic compounds present with the purified bisphenols. These color bodies develop over a period of time, particularly when trace amounts of iron are present to catalyze the oxidation. In an attempt to reduce such oxidations, additives such as sodium phosphate and phthalic anhydride have been added to bisphenols. Although these additives may delay the formation of color bodies with their consequent discoloration of the bisphenol composition, discoloration eventually occurs.

We have now found that bisphenol composition, particularly bisphenol-A, can be stabilized against the formation of some color bodies and consequent discoloration by controlling their iron content. The reduction or elimination of color changes in the product over periods of time is an economic advantage, and for many applications imperative. For example, when the bisphenol is to be used in the synthesis of polymers requiring color standards.

SUMMARY OF THE INVENTION

The invention comprises, a method of color stabilizing bisphenol compositions, which comprises;
admixing with the bisphenol a color-stabilizing proportion of an α-hydroxy polycarboxylic acid iron sequestrant.

The invention also comprises the bisphenol compositions which are color-stabilized by the process of the invention.

DETAILED DESCRIPTION OF THE PREFERRED EMBODIMENTS OF THE INVENTION

As described above, there are a wide variety of known processes for the preparation of bisphenols, generally by condensing 2 moles of phenol starting reactant with a carbonyl compound. The present invention may start with the product of such a process, generally following conventional and known procedures for separation and purification of the final bisphenol product.

In the commercially important processes for producing bisphenols, there is generally included purification procedures for isolating the desired product in relatively pure form. Since the reactor temperatures may be within the range of from about 40° C. to 95° C. the crude product stream presents the bisphenol in molten form. The crude product may be withdrawn from the reactor continuously and fed continuously to purification procedures. For example, in the commercial production of bisphenol-A the crude product may be treated to remove acidic impurities and filtered to remove particulates (e.g. ion exchange resin particles, metal fragments, etc.). The filter will generally remove particles having a size greater than about 5 microns. Distillation in a series of distillation columns follows each of which operate under progressively (sequentially) higher vacuum/temperature conditions than the preceding column in order to separate the stream.

Advantageously, the present invention is practiced by adding to the third fraction, the purified bisphenol, just prior to crystallization, a color stabilizing proportion of an α-hydroxy polycarboxylic acid sequestering agent.

Representative of the α-hydroxy polycarboxylic acids are those of the formula:

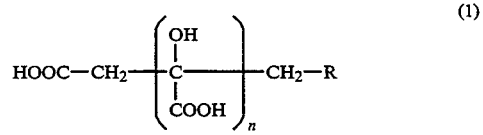

(1)

wherein n=1–3 and R is a carboxyl or a hydroxyl group, preferably a carboxyl group. Within the scope of the formula (I) given above are citric acid and tartaric acid both of which will combine with metal ions such as ferric or ferrous ions to form stable metal complexes. Citric acid is most preferred. Unexpectedly, small proportions of these sequestering agents do not adversely affect the product bisphenols, but by removing the metal ions, apparently inhibit the formation of color bodies and discoloration of the composition. It is unexpected, because acids have previously been implicated in the discoloration of bisphenol compositions.

A color-stabilizing proportion of the sequestering agent is generally within the range of from about 0.001 to 300 ppm of the bisphenol-A, by weight. Higher proportions may be admixed with the bisphenol-A, but generally are not necessary.

Admixture of the α-hydroxy polycarboxylic acid with the bisphenol is advantageously carried out by metering in the required proportion while the bisphenol is in a molten state, so the additive remains in close association when the bisphenol is crystallized for storage. The admixture can be continuous, or by batch procedures.

The following examples and preparations describe the manner and process of making and using the invention and set forth the best mode contemplated by the inventors of carrying out the invention are not to be construed as limiting the invention.

Example 1 (Control)

A quantity of bisphenol-A having an Fe content of approximately 0.1 to 10 ppm and a purity of more than 99.9% was obtained and tested to determine its final absorbance (FA) by colormetric analysis. The sample was then heated to a temperature of 350° F. for a period of 6 hours. During this time, aliquots were taken and tested for FA. The test results are set forth in the Table 1 below.

Example 2 (Comparative Example)

The procedure of Example 1, supra., was repeated, except that the quantity of bisphenol-A was first treated by the addition of 150 ppm of phthalic anhydride as a color stabilizer. The test results are set forth below in the Table 1.

Example 3 (Invention)

The procedure of Example 1, supra., was repeated, except that the quantity of bisphenol-A was first treated by the addition of 150 ppm of citric acid as a color stabilizer. The rest results are set forth below in the Table 1.

TABLE 1

| | BPA FINAL ABSORBANCE | | |
|---|---|---|---|
| EXAMPLE Time (min) | CONTROL 1 | PHTHALIC ANHYDRIDE 2 | CITRIC ACID 3 |
| 0 | 0.124 | 0.155 | 0.109 |
| 120 | 0.183 | 0.184 | 0.114 |
| 180 | 0.18 | 0.197 | 0.113 |
| 240 | 0.209 | 0.17 | 0.117 |
| 300 | 0.154 | 0.194 | 0.135 |
| 360 | 0.237 | 0.289 | 0.111 |

From the Table 1 above, it can be seen that after six hours, the citric acid treated bisphenol (Example 3) showed a stabilizing effect in respect to the FA determination, whereas the control (Example 1) showed significant increase after only 5 hours.

The final absorbance (FA) determination is a thermal stability test for Bisphenol-A(BPA). It involves dissolving 5 grams of BPA in 50 ml of methanol after the BPA has been heat aged in an oven at 140° C. for 5 hours. The absorbance is then measured at 350 nm with pure methanol as the absorbance reference.

We claim:

1. A method of color-stabilizing crystallized bisphenol compositions, which comprises;
   admixing with the molten bisphenol after distillation but before crystallization a color-stabilizing proportion of an α-hydroxypolycarboxylic acid iron sequestrant.

2. The method of claim 1 wherein the bisphenol is bisphenol-A.

3. The method of claim 1 wherein the α-hydroxy polycarboxylic acid is of the formula:

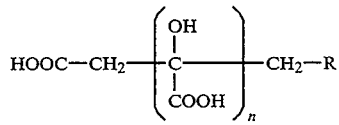

wherein n is an integer of 1 to 3 and R is selected from hydroxyl and carboxyl groups.

4. The method of claim 3 wherein R is carboxyl.

5. The method of claim 4 wherein the polycarboxylic acid is citric acid.

6. The method of claim 1 wherein a color-stabilizing proportion is within the range of from about 0.001 to 300 ppm of the bisphenol.

7. Color stabilized bisphenol composition which comprises:
   a crystallized bisphenol in admixture with a color-stabilizing proportion of an α-hydroxypolycarboxylic acid added to the molten bisphenol just prior to crystallization.

8. The composition of claim 7 wherein the bisphenol is bisphenol-A.

9. The composition of claim 8 wherein the α-hydroxypolycarboxylic acid is citric acid.

* * * * *